US009289349B2

(12) United States Patent
Doochin et al.

(10) Patent No.: US 9,289,349 B2
(45) Date of Patent: Mar. 22, 2016

(54) SOUND THERAPY SYSTEMS AND METHODS FOR RECALIBRATING THE BODY'S ELECTROMAGNETIC FIELD

(71) Applicant: URIEL PATENT, LLC, Franklin, TN (US)

(72) Inventors: Lawrence L. Doochin, Franklin, TN (US); Janice L. Doochin, Franklin, TN (US); Susan E. Whitehawk, Cottonwood, AZ (US); Gregg Tauriello, Cornville, AZ (US)

(73) Assignee: URIEL PATENT, LLC, Franklin, TN (US)

( * ) Notice: Subject to any disclaimer, the term of this patent is extended or adjusted under 35 U.S.C. 154(b) by 97 days.

(21) Appl. No.: 14/165,550

(22) Filed: Jan. 27, 2014

(65) Prior Publication Data

US 2014/0276193 A1 Sep. 18, 2014

Related U.S. Application Data

(60) Provisional application No. 61/787,060, filed on Mar. 15, 2013.

(51) Int. Cl.
A61H 23/02 (2006.01)
A61H 23/00 (2006.01)
(Continued)

(52) U.S. Cl.
CPC ............ *A61H 23/0245* (2013.01); *A61H 23/00* (2013.01); *A61M 21/00* (2013.01);
(Continued)

(58) Field of Classification Search
CPC ............ A61H 23/00; A61H 2023/002; A61H 23/004; A61H 23/006; A61H 23/02; A61H 2023/0209; A61H 23/0218; A61H 2023/0227; A61H 23/0236; A61H 23/0245; A61H 2201/1207; A61H 2201/16; A61H 2201/1604; A61H 2201/1607; A61H 2201/1642; A61H 2201/164; A61H 2201/1635; A61H 2201/1638; A61H 2201/165; A61H 2201/5005; A61H 39/002; A61H 2230/655; A61M 21/02; A61M 21/00; A61M 2021/0022; A61M 2230/65; A61M 2021/0072; A61M 2021/002
USPC .......................................................... 601/47
See application file for complete search history.

(56) References Cited

U.S. PATENT DOCUMENTS 1,753,312 A * 4/1930 Nicolson ....................... 381/162
1,973,673 A * 9/1934 Rice .............................. 181/123
(Continued)

FOREIGN PATENT DOCUMENTS

JP 2009148521 A 7/2009
KR 1020090011993 A 2/2009
WO 2009076250 A1 6/2009

OTHER PUBLICATIONS

International Search Report issued Jul. 3, 2014 in connection with corresponding PCT App. No. PCT/US2014/026626.
(Continued)

Primary Examiner — Valerie L Woodward
Assistant Examiner — Tu Vo
(74) Attorney, Agent, or Firm — Baker Donelson

(57) ABSTRACT

A sound treatment system includes an audio system for transmitting tones of predetermined frequencies through a plurality of outputs. A sound transmitting device is electrically connectable to one or more of the outputs, and includes a speaker for transmitting the tones received. The speaker is adjacent to crystal which is vibrationally responsive to the tones. A method of using the system includes generating tonal segments of predetermined duration, modulating the frequencies, and compiling these into an audio program. One or more sound transmitting devices are placed on desired locations of the body, and their inputs connected to corresponding outputs of the audio system. The generating step includes compiling selected predetermined frequencies into an audio program to generate the tonal segments, as well as modulating tones of one or more desired frequencies to generate the tonal segments.

13 Claims, 4 Drawing Sheets

(51) Int. Cl.
    *A61M 21/00* (2006.01)
    *A61M 21/02* (2006.01)
    *A61H 39/00* (2006.01)

(52) U.S. Cl.
    CPC ............ *A61M 21/02* (2013.01); *A61H 23/006* (2013.01); *A61H 23/02* (2013.01); *A61H 23/0218* (2013.01); *A61H 23/0236* (2013.01); *A61H 39/002* (2013.01); *A61H 2023/0227* (2013.01); *A61H 2201/16* (2013.01); *A61H 2201/5005* (2013.01); *A61H 2230/655* (2013.01); *A61M 2021/0022* (2013.01); *A61M 2021/0027* (2013.01); *A61M 2021/0072* (2013.01); *A61M 2230/65* (2013.01)

(56) References Cited

U.S. PATENT DOCUMENTS

| | | | | |
|---|---|---|---|---|
| 3,505,461 A | * | 4/1970 | Omura | G10H 1/08 84/698 |
| 8,907,191 B2 | * | 12/2014 | Seese et al. | 84/603 |
| 2006/0222199 A1 | * | 10/2006 | Abe et al. | 381/396 |
| 2007/0217644 A1 | * | 9/2007 | LeDonne | 381/396 |
| 2008/0101621 A1 | * | 5/2008 | Zimmerman | 381/61 |
| 2008/0125620 A1 | * | 5/2008 | McNew | 600/27 |
| 2009/0076421 A1 | * | 3/2009 | Grant, Jr. | 601/47 |
| 2009/0204034 A1 | * | 8/2009 | May | 601/15 |
| 2010/0320819 A1 | | 12/2010 | Cohen et al. | |
| 2011/0152729 A1 | | 6/2011 | Oohashi et al. | |
| 2011/0162505 A1 | * | 7/2011 | Parish | 84/189 |
| 2012/0051579 A1 | * | 3/2012 | Cohen | A61H 23/0236 381/388 |
| 2012/0172676 A1 | | 7/2012 | Penders et al. | |

OTHER PUBLICATIONS

Written Opinion issued Jul. 3, 2014 in connection with corresponding PCT App. No. PCT/US2014/026626.

* cited by examiner

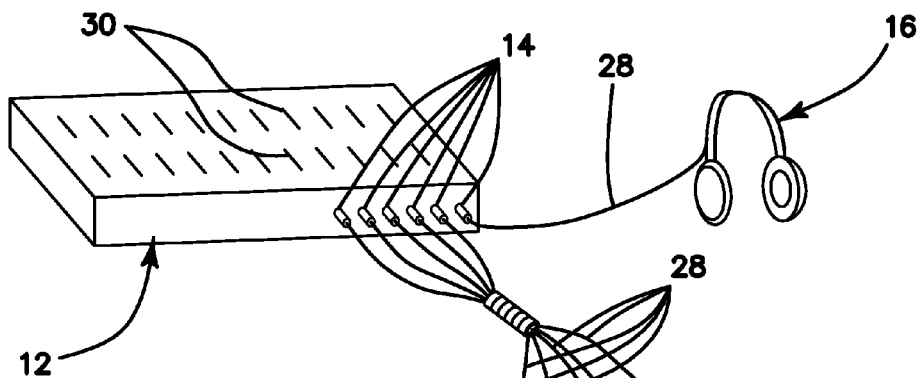
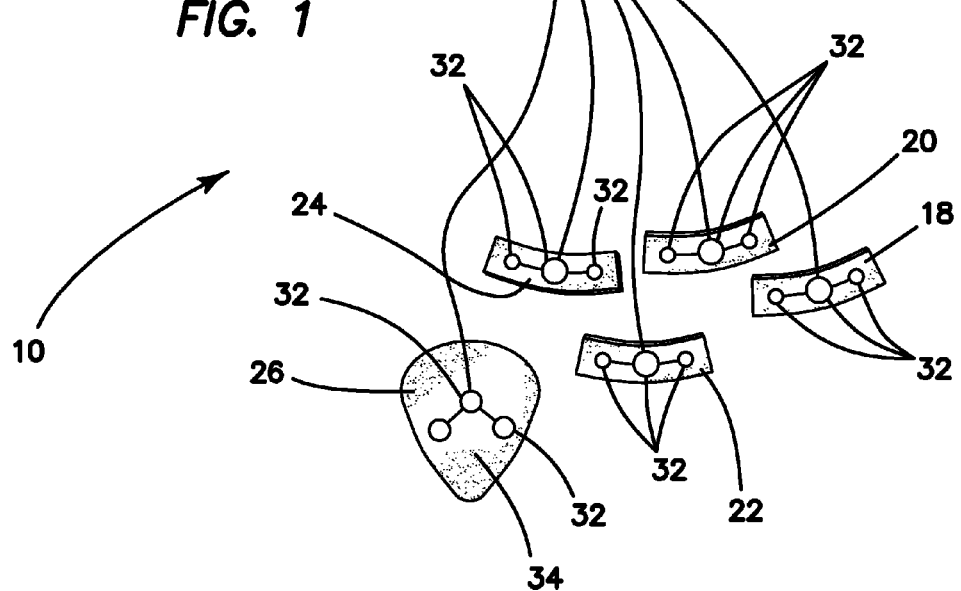
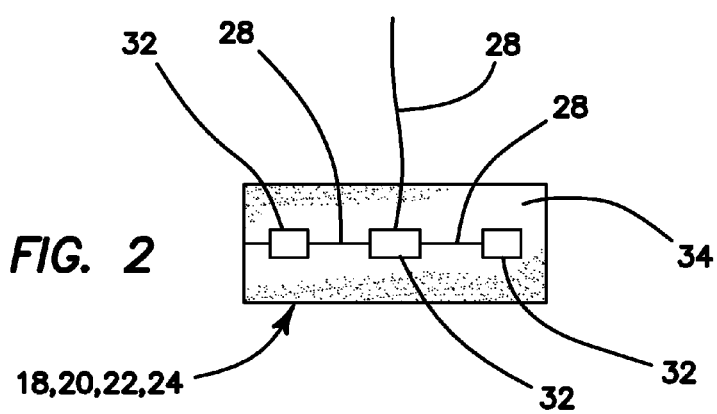
FIG. 1
FIG. 2

SOUND THERAPY SYSTEMS AND METHODS FOR RECALIBRATING THE BODY'S ELECTROMAGNETIC FIELD

This application claims the benefit under 35 U.S.C. 119(e) of the filing date of Provisional U.S. Application Ser. No. 61/787,060, entitled Systems and Methods for Balancing Body Electromagnetic Levels, filed on Mar. 15, 2013, which application is herein expressly incorporated by reference, in its entirety.

BACKGROUND OF THE INVENTION

In the past number of years, particularly since the sharp rise in personal electronic communications devices and other technology, it is documented that there has been a significant increase in electromagnetic emissions. Also documented has been a large increase in toxic heavy metal and chemical residues in our air, soil, water, and food from pesticides, herbicides, radioactive materials, and the like. Our bodies are electromagnetic fields that are greatly scrambled and affected by the signals put out by technology, and heavy metals have their own electromagnetic frequencies which further disrupt the body's natural field. With a disrupted, electromagnetic field and increased levels of toxicity that we are exposed to, the body's immune system weakens and signs of disease and health related issues increase. The inventors believe that specific metals are causing sensitivity to specific electromagnetic waves from cell towers, modems, computers, phone handsets, and the like, thus emerging as physical and emotional ailments not diagnosable or treatable through traditional treatments.

It would be advantageous to have a protocol using a more effective system for detoxifying the body from heavy metals than what currently exists, in order to recalibrate the body's electromagnetic field, but there also exists a great need to recalibrate the body's electromagnetic field as the metals are removed.

SUMMARY OF THE INVENTION

The inventive device, in certain embodiments, comprises a single, high grade crystal disk which has been suspended over a speaker. Human toning has been recorded and broken into individual frequency snippets, then looped to be in one minute segments. A frequency analyzer is used to determine the dominant frequency and harmonic frequencies of each segment.

Three signal generators are set up in an audio playback software program so that all three of the generated tones are able to run simultaneously and their outputs are able to combine with the segment.

One of the signal generators is tuned as closely as possible to the same frequency as the dominant frequency of the segment. The signal generator's various waveform types (sine, square, triangle, sawtooth) are previewed to cause the crystal in the device to resonate with sympathetic vibration. A next step is to sweep through all of the frequency ranges to find any resonant frequencies to the dominant or harmonic frequencies of the segment. Multiples and divisions of the dominant and/or the harmonic frequency of the segment can be used as starting points. As an example, if the dominant or any of the harmonic frequencies is 500 Hz, divisions such as 25 and 125 Hz can be experimented with. Multiples of the harmonic frequencies, such as 1000, 2000, or 4000 Hz may also be the subjects of experimentation. If no resonance is found using one signal generator, second and third generators can be added as well. It is important to maintain even harmonics and to avoid odd harmonics.

The goal is to create combinations of frequencies that sympathize with a particular vocal segment, so as a particular frequency snippet is transmitted, it creates a vibration in the crystal in an effort to produce a piezoelectric effect, which is defined as being the generation of an electric charge in certain nonconducting materials, such as quartz crystals and ceramics, when they are subjected to mechanical stress such as pressure or vibration. All matter in the universe vibrates and creates a sound, even if that sound is outside of the hearing range of the human ear. Once the crystal vibrates, it greatly enhances the sound from the human tone, creating a heightened effect which is then powerfully transmitted to the body through a supercharged electrical current via the piezoelectric effect.

Once each frequency snippet has been uniquely modulated to create the sympathetic vibration in the crystal, there is a master audio program created which contains each of these modulated frequencies, further enabling a customized program to be created for each client. This customized program is created by the client listening to each individual toning frequency while electrodermal screening or muscle testing is conducted to find the frequencies which are most balancing to that client's body at the time. Then those frequencies are compiled into their own audio program to be listened to through headphones and to be transmitted through the pads of the device.

The toning sounds may be delivered continuously or in a pulse. The sounds may be delivered to all of the pads of the system simultaneously, or sequentially, through the various pads in the system. Another alternative is to only deliver the sounds to some of the system pads, for example, like the left side only or applied to areas of the body affected by a stroke, or the like.

Customized audio programs may be created for the headphones as well. This process involves a separate blend or mix of segment and signal generators, with loudness created for headphone playback. This separate mix is necessary since the frequencies chosen to vibrate the crystal in the device may be unpleasant, too loud, or contain odd harmonics and/or frequencies that may cause damage to human hearing during playback through headphones.

Acoustical effects are applied sparingly to the segment, as needed (exciter, reverberation, ambiance, etc.). Delay and chorus effects are avoided.

Headphone programs differ from device programs in at least the following ways:
1. The mix is produced in stereo and preserves the acoustical effects;
2. Odd harmonics are reduced in volume or eliminated;
3. Stereo imaging becomes an additional parameter; and
4. Overall volume is set not to exceed minus twenty (−20) decibels.

The stereo segment is summed to mono for the programming of the devices.

The applications for a system of this type are practically endless. In addition to the use of such a system to recalibrate the body's electromagnetic field once metals are removed, other exemplary uses include the alleviation of anxiety/panic disorders, stress, sleep disorders, addictions, brain wave stabilization, stroke rehabilitation/coordination, nerve damage, accelerating healing of bone fractures, increasing the ability of senses such as hearing, and the like. This technology may be used on a larger scale (larger speaker and crystal assembly)

to create a peaceful atmosphere in a room through a speaker that houses the device components.

More particularly, there is provided a sound treatment system, which comprises an audio system for transmitting tones of predetermined frequencies through a plurality of outputs. A sound transmitting device is electrically connectable to one or more of the outputs, wherein the sound transmitting device comprises one of a speaker or piezo transducer for transmitting the tones received from the audio system output. The speaker is adjacent to crystal which is vibrationally responsive to the tones. Attachment structure is provided for attaching the sound transmitting device to a desired body location, such that the vibrating crystal is adapted to treat a pulse point at the desired location. This attachment structure comprises pads, or perhaps sports wrap, a pouch having straps attached thereto, or other suitable means.

The audio system preferably comprises a sound board. The system may also comprise headphones electrically connectable to one of the outputs. A plurality of the sound transmitting devices are preferably provided, for attachment to ankles, wrists and/or other desired locations of the body.

The audio system generates tones having different modulated toning frequencies and the outputs are capable of delivering the same or different modulated toning frequencies.

The crystal, in some embodiments, comprises a plurality of crystal disks assembled together in a stack. The speaker or piezo transducer is disposed in the stack comprising a plurality of speakers or piezo transducers. In other embodiments, the crystal may comprise crystal granules. In one disclosed embodiment, the crystal is suspended over the speaker or piezo transducer. In this embodiment, polyfilm may be utilized to secure the crystal to the speaker or piezo transducer in the aforementioned suspended state.

An audio program is provided for generating tones of predetermined and customized toning frequencies for transmission through the outputs of the audio system, the toning frequencies previously having been looped into one minute segments and modulated through differing combinations of a signal generator's waveform in order to create a harmonic resonance and sympathetic vibration in the crystal, with a master audio program created that can be used to create a custom audio file for each client when they are tested. The crystal, in turn, creates a frequency as it vibrates which correspondingly enhances the originally received toning frequency while also producing a piezoelectric current. The enhanced toning frequency and piezoelectric current together cause a corresponding harmonic response in targeted organs and tissues of the body on which the sound transmitting device carrying the crystal is disposed, by delivery of a supercharged electrical signal through acupuncture pulse or meridian points of the body, rebalancing the compromised electromagnetic field of the body and returning the system to optimum performance.

A headphone amplifier is connectable to one of the outputs, the headphone amplifier having a plurality of outputs which are connectable to the plurality of sound transmitting devices.

The crystal may comprise one or more of clear quartz, rose quartz, fluorite, tourmaline and ceramic. The toning frequencies may be delivered to the sound transmitting device in either a continuous or pulsed mode, and also may be delivered to the sound transmitting devices either simultaneously or sequentially. Separate sound generating programs may be provided for delivery of different generated tones to each of the sound transmitting device and the headphones.

In another aspect of the invention, there is provided a sound transmitting device for use in a sound treatment system which comprises an audio system for transmitting tones of predetermined and customized toning frequencies for transmission through the outputs of the audio system, the toning frequencies having previously been looped into one minute segments and modulated through differing combinations of a signal generator's waveform, which could be one or more of a sine wave, square wave, triangle wave, or sawtooth wave, in order to create a harmonic resistance and sympathetic vibration in the crystal, with a master audio program created that can be used to create a custom audio file for each client when they are tested with electrodermal screening or muscle testing. The sound transmitting device comprises one of a speaker or piezo transducer for transmitting the tones received from the audio system output. The speaker is disposed adjacent to crystal which is vibrationally responsive to those tones. Attachment structure for attaching the sound transmitting device and crystal to a desired body location is also provided, such that the vibrating crystal is adapted to treat a pulse point at the desired location. Preferably, in one embodiment, the crystal is suspended over the speaker or piezo transducer and polyfilm is utilized to secure the crystal to the speaker or piezo transducer in that suspended state.

In still another aspect of the invention, there is provided a sound treatment system which comprises an audio system comprising a plurality of outputs, and a sound transmitting device electrically connectable to one or more of the outputs of the audio system, wherein the sound transmitting device comprises one of a speaker or piezo transducer for transmitting tones received from the audio system outputs. The speaker is disposed adjacent to crystal which is vibrationally responsive to these generated tones. An audio program is provided for generating tones of predetermined and customized toning frequencies previously having been looped into one minute segments and modulated through differing combinations of a signal generator's waveform, which could be one or more of a sine wave, square wave, triangle wave, or sawtooth wave, in order to create a harmonic resonance and sympathetic vibration in the crystal, with a master audio program created that can be used to create a custom audio file for each client when they are tested. The toning frequencies are transmitted through the crystal in order to create a harmonic resonance and sympathetic vibration in the crystal, the crystal in turn creating a frequency as it vibrates, which correspondingly enhances the originally received toning frequency while also producing a piezoelectric current. The enhanced toning frequency and piezoelectric current together cause a corresponding harmonic response in targeted organs and tissues of the body on which the sound transmitting device carrying the crystal is disposed by delivery of a supercharged electrical signal through acupuncture pulse or meridian points of the body, rebalancing the compromised electromagnetic field of the body and returning the system to optimum performance. The tones preferably comprise human tones, more particularly singing, and may be delivered continuously or in pulses.

In still another aspect of the invention, there is described a method of using a sound treatment system comprising an audio system for transmitting tones of a predetermined frequency or frequencies, having previously been looped into one minute segments and modulated through differing combinations of a signal generator's waveform in order to create a harmonic resonance and sympathetic vibration in the crystal, through one or more outputs and one or more sound transmitting devices electrically connectable to corresponding ones of the outputs, locating one or more of the sound transmitting devices in proximity to one or more corresponding desired locations on the clients body, and connecting inputs of the sound transmitting devices to corresponding ones of the outputs of the audio system, wherein each of the one or more sound transmitting devices comprises one of a speaker or piezoelectric transducer and adjacent crystal.

The inventive method may further comprise a step of assessing a client in a preliminary session to determine which individual sound frequencies are most balancing for the particular client's body, working from the master audio program that has each of the modulated toning frequencies. This assessing step is performed by testing the client's response using one of electrodermal screening, applied kinesiology, or muscle reflex testing. Other known types of testing bodily response may be used as well.

In currently preferred approaches, the predetermined length of each generated tonal segment is approximately one minute, and the generated tonal segments are comprised of human tones.

The invention, together with additional features and advantages thereof, may best be understood by reference to the following description taken in conjunction with the accompanying illustrative drawing.

BRIEF DESCRIPTION OF THE DRAWINGS

FIG. 1 is a schematic view of a sound treatment system constructed in accordance with the principles of the present invention;

FIG. 2 is a schematic view of one sound transmitting device constructed in accordance with the principles of the present invention;

DESCRIPTION OF THE PREFERRED EMBODIMENT

Figure 3:
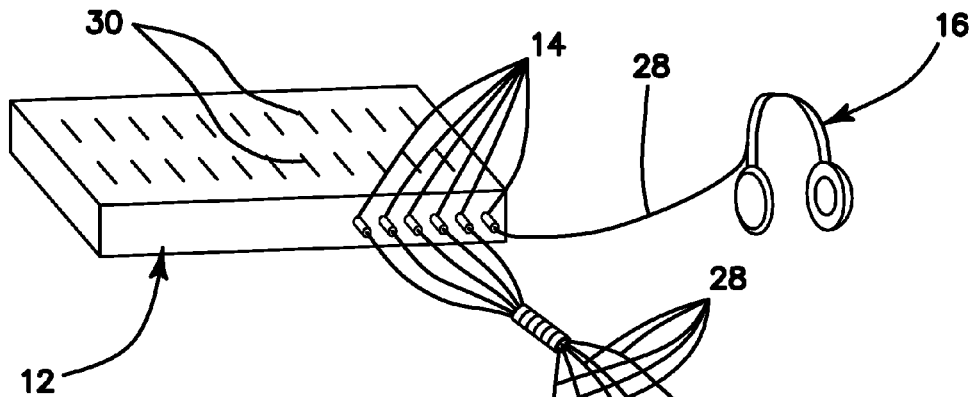
FIG. 3 is a schematic view similar to FIG. 1 illustrating a modified embodiment of the sound treatment system.

Now with reference more particularly to FIG. 1, there is illustrated one embodiment of a sound treatment system 10 constructed in accordance with the principles of the present invention, for use generally in treatment of the type herein described, and for use particularly in treatment protocols described herein, including, but not limited to, Examples 1, 2, and 3. The system 10 includes a soundboard or audio system 12, which includes jacks 14 for output to headphones 16 and a plurality of sound transmitting devices 18, 20, 22, 24, and 26, through wires 28. In one particular embodiment, the audio system 12 may comprise a known product made by Avid and marketed under the trademark Pro Tools+Mbox® Pro, but other suitable audio systems may be used as well. The headphones 16 are worn by the client during a sound therapy session. The sound transmitting devices 18, 20, 22, 24, 26 include fabric or pads, strapping, and/or other suitable attachment structure for comfortable attachment to the body and are worn, respectively, on both ankles, both wrists, and the back of the client. The sound transmitting device 26 is adapted for disposition on the middle to lower portion of the back, for supporting the endocrine system. Modulated toning frequencies are delivered to each sound transmitting device. Each output has the capability of delivering an individualized toning frequency based on a client's needs. Toning frequency adjustments may be made using individualized modulation controls 30 on the sound board 12, or automatically using pre-programmed computerized controls. The sound transmitting devices 18, 20, 22, 24, an exemplary one of which is illustrated in more detail in FIG. 2, are made, in this illustrated embodiment, with a nonflammable insulated material and preferably comprise three small flat speakers 32 that are placed in crushed lab grown pure quartz crystal 34, having piezoelectric qualities, though of course, the number and type of speakers, and the material from which the devices are made may vary. The sound transmitting device 26 for the back is similar in construction to the wrist and ankle devices, except that it is not designed to surround the back, but rather to lay on it. The crystal granules 34 is secured within the devices by suitable means, such as by being sewn into pockets of the devices, surrounding each speaker 32.

The sound board 12, as noted above, controls the modulated sound frequency that is delivered to the speakers within the sound transmitting devices. These speakers transmit human voiced toning recordings with different frequency modulations that are attuned to the body's natural or non-diseased electromagnetic frequency. This human toning may comprise singing. Software instructs the sound board how to distribute the tones and through which outputs. Toning frequencies may be the same or different out of each output, depending upon needs and application.

In more particular detail, a method of transmitting modulated sound frequency tones to the inventive device involves combining human toning, broken down into individual frequencies and looped in segments of particular desired duration—in one specific approach these loops are approximately one minute in length. These loops or segments are modulated to create a vibration in the crystal, enhancing the original tone and delivering that enhanced tone to acupuncture points via an electrical signal generated by the device using the piezoelectric effect.

As noted above, the sound vibrates the crushed quartz crystal 34, creating a piezoelectric effect and generating a supercharged electromagnetic current. This current or electricity frequency recalibrates the body's electromagnetic field through the acupuncture pulse points on which the sound transmitting devices have been placed. The frequency delivered in a megahertz is determined at the beginning of the client session by an assessment, which, in a preferred approach, utilizes electrodermal screening (EDS) to determine which of the individual sound frequencies are most balancing or called for by the body. The best ones are compiled into the above mentioned audio program, using Pro-Tools or another suitable system, so that they are generated to create the aforementioned tonal loops. The time delivered also varies per frequency ranging from five minutes to an hour, though most sessions are thirty minutes or less.

Figure 4:
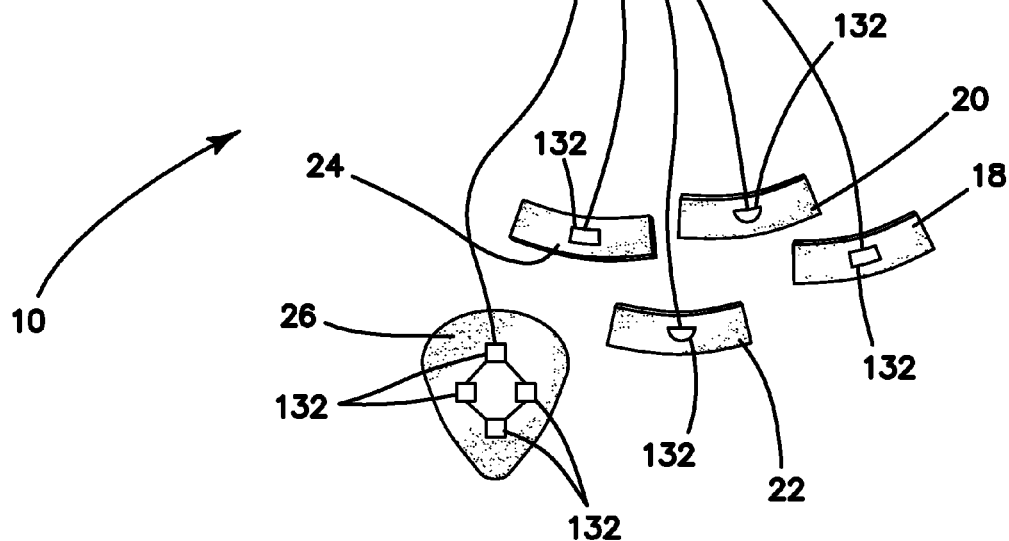
FIG. 4 is a schematic view similar to FIG. 3, illustrating a modified sound transmitting device.
Figure 4:
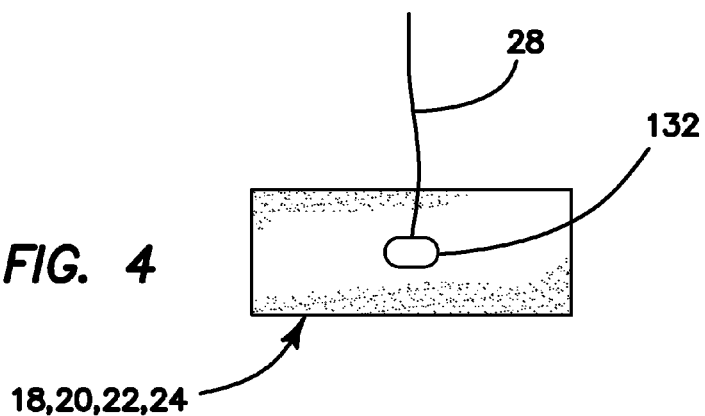

In an alternative approach, illustrated in FIGS. 3 and 4, a modified embodiment of the sound transmitting devices is shown and described. Like elements to both the systems of FIGS. 1 and 3 are denoted by identical reference numerals. The only substantial difference between the two embodiments is in the construction of the sound transmitting devices 18, 20, 22, 24, and 26. Instead of using granulated crushed crystal 34, as in the first embodiment, thin, lab grown high grade optical grade crystal disks are utilized. Specifically, in each wrist and ankle device 18, 20, 22, 24, a stack 132 is disposed, comprising a speaker, attached to the wire 28, and four crystal disks stacked on the speaker, one atop the other, like lifesavers. There is one stack 132 disposed on each wrist and ankle sound transmitting device, as shown, so that the crystal disk on an opposed end of the stack 132 relative to the speaker rests against a pulse point on the client's body. The stacked disks and speaker are held together with pure copper wire, and they are in a carrier of ground high grade crystal shards, like sand.

The back device 26 had 8 crystal disks, in four stacks of two disks each, plus a speaker, as in the ankle and wrist devices, spaced across the device.

Of course, while the illustrated embodiment includes one stack of four disks in each wrist and ankle device, and four stacks of two disks in the back device, the numbers of stacks and disks in each stack may be varied for each device, and the location of each device may also be varied, within the scope of the present invention. Also, while high grade lab-grown crystal is preferred, other types of suitable crystals that are not man-made, including rough natural crystals, may be used as well.

The functionality of this modified embodiment is otherwise much like that in the first embodiment. The speaker in each crystal disk stack vibrates and resonates the crystal in the stack, creating a piezoelectric effect and generating a supercharged electromagnetic current. This current or electricity frequency recalibrates the body's electromagnetic field through the acupuncture pulse points on which the sound transmitting devices, and particularly the stacks 132, have been placed. The particular toning frequency delivered is determined at the beginning of the client session by electrodermal screening.

Figure 5:
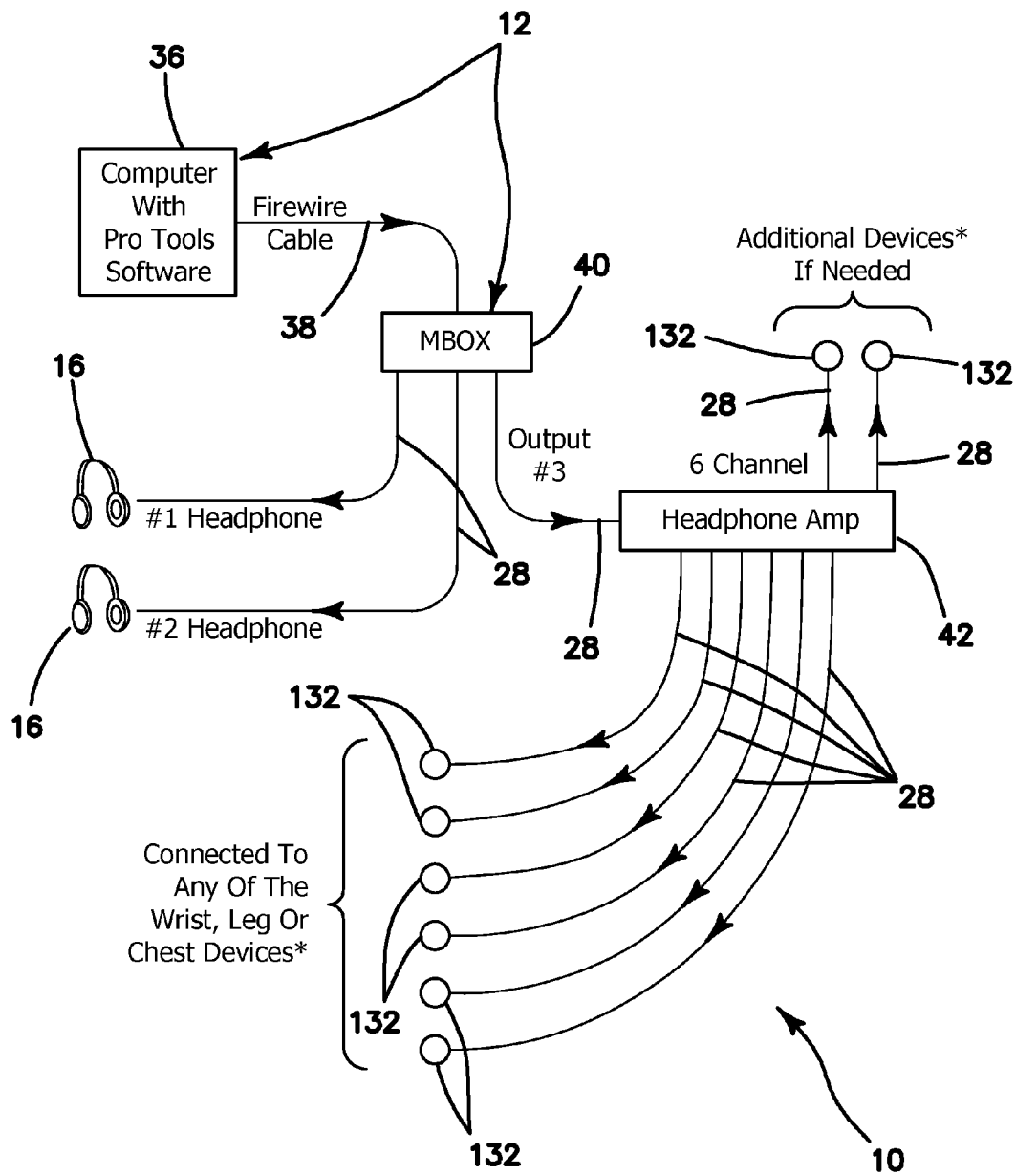
FIG. 5 is a schematic view similar to FIGS. 1 and 3, illustrating still another modified embodiment of the sound treatment system of the present invention.

Referring now to FIG. 5, there is shown yet another embodiment of a sound treatment system 10 constructed and designed in accordance with the principles of the present invention. Again, with respect to this embodiment, like elements to those shown in the other embodiments of FIGS. 1 and 3 are denoted by identical reference numerals, for consistency. Thus, the system 10 is comprised of a soundboard or audio system 12, which is illustrated as including a computer 36 loaded with ProTools software and connected via a firewire 38 to an audio interface 40, which may be purchased as a unit from Avid under the trademark MBOX. Output wires 28 connect the audio interface 40 to one or more headphones 16, and also to a headphone amplifier 42. The headphone amplifier 42 has a number of output connections 28 which connect the amplifier to a corresponding plurality of stacks, or sound transmitting devices, 132, which will be described in more detail below. As discussed above, each sound transmitting device 132 may be secured to a pad or other suitable attachment structure for attaching them to desired parts of the body, such as wrist pads and straps, ankle pads and straps, and the like.

Figure 7:
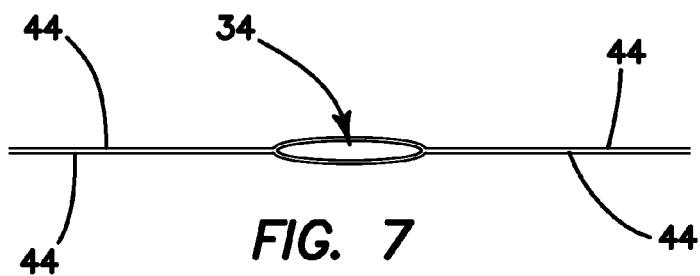
FIG. 7 is a side view of a crystal assembly usable with sound transmitting devices of the present invention.
Figure 8:
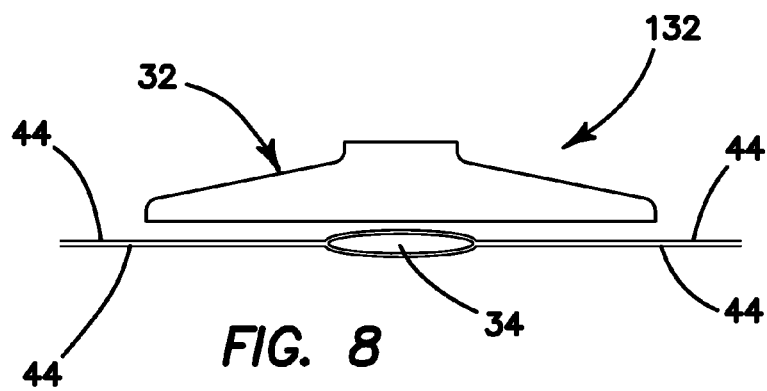
FIG. 8 is a side view of a modified embodiment of a sound transmitting device usable in the sound treatment systems of the present invention, and particularly the system illustrated in FIG. 5.

Now, with reference to FIGS. 6-8, one configuration of the device 132 will be described in greater detail. In the illustrated embodiment, the device 132 comprises a crystal 34 which is suspended over a speaker transducer 32. FIG. 7 illustrates the manner by which the crystal 32 is suspended, using two layers 44 of polyfilm or other suitable material. In one embodiment, the polyfilm has a thickness of 1.2 mil. The polyfilm 44 holding the crystal 34 in place is wrapped around the back side of the speaker 32. Once the unit 132 is assembled, it is wrapped with professional sports wrap to hold all of the components in place, and to provide a way to attach the unit to a user's wrist, ankle, or other suitable location. Alternatively, the housing holding the speaker and the crystal may be put in a thin silk pouch which has Velcro straps attached thereto, so that it can easily be wrapped around a wrist or ankle.

Figure 6:
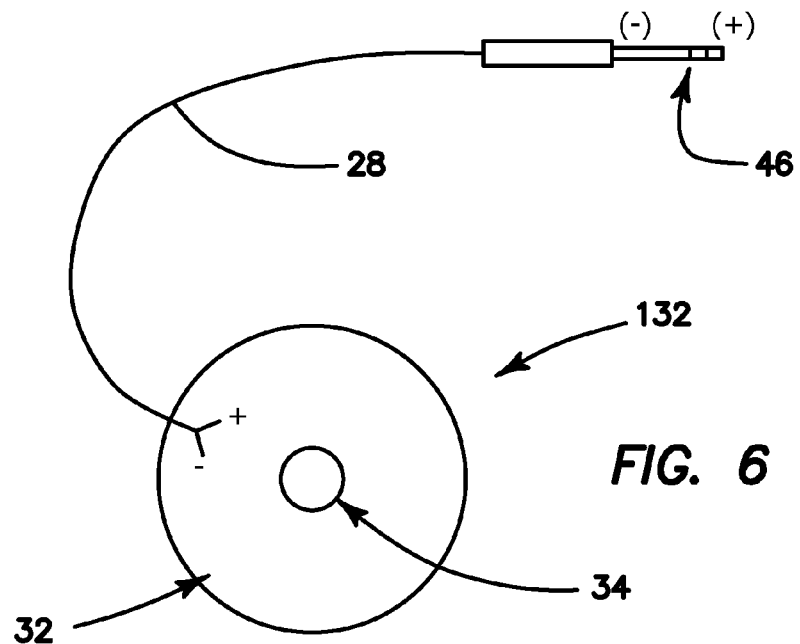
FIG. 6 is a schematic view of a modified embodiment of a sound transmitting device usable, for example, in any of the sound treatment systems of the present invention.

As illustrated in FIG. 6, the speaker 32 is electrically attached to a wire 28, which has at its other end thereof a ¼ inch TRS plug for insertion into a jack in the headphone amplifier 42 or other suitable power source.

Other possible embodiments for the sound transmitting devices and accompanying pad assemblies may include, for example, a band configured to contain sand or another padding and insulative material surrounding a pocket for containing a speaker, wherein a thin copper interface is disposed in the pocket adjacent to the speaker and exposed to the exterior of the band. A speaker wire is connected to the speaker in the same manner as discussed in connection with the other embodiments, and functionality is similar, in that the speaker is driven to cause resonance in the thin copper interface. The device may comprise a piezo transducer as an alternative to a speaker. Clear quartz crystal may be used, or, alternatively, other minerals such as amethyst, rose quartz, fluorite, tourmaline, and the like could be used. Each of these materials has its own unique electromagnetic signature/frequency which gives off certain qualities—e.g. one may give a peaceful feeling.

As described above, audio programs for the device 132 may be created by a process which is begun by recording a human voice singing at various pitches. Computer toning, musical instruments, nature sounds, etc. may be utilized instead of a human voice, but the remaining description will assume the use of a human voice. A short portion of the recording (approximately one second or less) is looped or duplicated multiple times to create about a one minute segment or loop. A frequency analyzer is used to determine the dominant frequency and harmonic frequencies of the segment.

Three signal generators are set up in an audio playback software program so that all three of the generated tones are able to run simultaneously and their outputs are able to combine with the segment. One of the signal generators is tuned as closely as possible to the same frequency as the dominant frequency of the segment. The signal generator's various waveform types (sine, square, triangle, sawtooth) are previewed to cause the crystal in the device to resonate with sympathetic vibration. A next step is to sweep through all of the frequency ranges to find any resonant frequencies to the dominant or harmonic frequencies of the segment. Multiples and divisions of the dominant and/or the harmonic frequency of the segment can be used as starting points. As an example, if the dominant or any of the harmonic frequencies is 500 Hz, divisions such as 250 and 125 Hz can be experimented with. Multiples of the harmonic frequencies, such as 1000, 2000, or 4000 Hz may also be the subjects of experimentation. If no resonance is found using one signal generator, second and third generators can be added as well. It is important to maintain even harmonics and to avoid odd harmonics.

Once each of the toning frequencies have been modulated, they are compiled into a master audio program and they are available to be used for customized testing with each client to determine which of the frequencies are most balancing for the body as the client listens through headphones and feels the effect through the pads. This prescreening is done as each client listens to each frequency while the electrodermal screening practitioner tests a meridian point on the body and obtains a reading indicating how balancing that particular frequency is. This may be achieved by a procedure known as "muscle testing", which is basically the body's automatic response to stimuli. The most balancing ones are compiled into a client specific and customized audio program, using ProTools or another suitable system.

The goal in modulation of the individual frequencies is to create combinations of waveforms that sympathize and have a resonance with a particular vocal segment so as to create a vibration in the crystal in an effort to produce a piezoelectric effect, which is defined as being the generation of an electric charge in certain nonconducting materials, such as quartz crystals and ceramics, when they are subjected to mechanical stress (such as pressure or vibration). The toning sounds may be delivered continuously or in a pulse. The sounds may be delivered to all of the pads in the system simultaneously, or sequentially, through the various pads in the system. Another alternative is to only deliver the sounds to some of the system pads, for example, those applied to areas of the body affected by a stroke, or the like.

Audio programs may be created for the headphones as well. This process involves a separate blend or mix of segment and signal generators, with loudness created for headphone playback. This separate mix is necessary since the frequencies chosen to vibrate the crystal in the device may be unpleasant, too loud, or contain odd harmonics and/or frequencies that may cause damage to the human hearing during playback through headphones.

Acoustical effects are applied sparingly to the segment, as needed, (exciter, reverb, ambience, etc.). Delay and Chorus effects are avoided.

Headphone programs differ from device programs in at least the following ways:

1. The mix is produced in stereo and preserves the acoustical effects;
2. Odd harmonics are reduced in volume or eliminated;
3. Stereo imaging becomes an additional parameter; and
4. Overall volume is set not to exceed minus (−20) decibels.

The stereo segment is summed to mono for the programming of the devices.

The time delivered also varies per frequency ranging from five minutes to an hour, though most sessions are thirty minutes or less.

The applications for a system of this type are endless. Exemplary ones include the alleviation of anxiety/panic disorders, stress, sleep disorders, addictions, brain wave stabilization, stroke rehabilitation/coordination, nerve damage, speeding up the healing of bone fractures, increasing the ability of senses such as hearing, and the like. Although the device disclosed herein has been created to use commercially with ProTools and an MBox, the device may also be configured to be portable and used with a software application (app) downloaded onto a smart phone, tablet computer, or the like, that scans the body, through electrodermal screening or other methods, to determine the appropriate frequencies to be given to the person, or determination of a customized program may be skipped and just a generally healthy frequency delivered. This technology may be used on a larger scale (larger speaker and crystal assembly), for example, to create a peaceful atmosphere in a room through a speaker that houses the device components.

While this invention has been described with respect to various specific examples and embodiments, it is to be understood that various modifications may be made without departing from the scope thereof. Therefore, the above description should not be construed as limiting the invention, but merely as an exemplification of preferred embodiments thereof and that the invention can be variously practiced within the scope of the following claims.

What is claimed is:

1. A sound treatment system, comprising:
one or more applications running on at least one processor and communicatively coupled to an audio board, the one or more applications analyzing frequencies of an audio segment to identify a dominant frequency and a harmonic frequency of the audio segment, the one or more applications generating at least one tone at one or more of the dominant frequency, the harmonic frequency, a multiple of the dominant frequency, and a multiple of the harmonic frequency, the one or more applications combining the audio segment and the at least one tone into an audio signal and transmitting the audio signal to the audio board;
the audio board for transmitting the audio signal through a plurality of outputs;
a sound transmitting device electrically connected to an output of the plurality of outputs, wherein the sound transmitting device comprises a speaker or piezo transducer for transmitting the audio signal received from the audio board, the speaker or piezo transducer being adjacent to crystal which is vibrationally responsive to the audio signal;
attachment structure for attaching the sound transmitting device to a desired body location, such that the vibrating crystal is adapted to treat a pulse point at the desired body location; and
the audio board transmitting the audio signal to the sound transmitting device through the output to create a harmonic resonance and a sympathetic vibration in the crystal, wherein the crystal creates as it vibrates an additional tone at a frequency, wherein the vibrating crystal also produces a piezoelectric current, wherein the audio signal, the additional tone and the piezoelectric current together cause a corresponding harmonic response in targeted organs and tissues of the body on which the sound transmitting device carrying the crystal is disposed by delivery of a supercharged electrical signal through acupuncture pulse or meridian points of the body.

2. The sound treatment system as recited in claim 1, wherein the attachment structure comprises pads.

3. The sound treatment system as recited in claim 1, and further comprising headphones electrically connectable to the plurality of outputs.

4. The sound treatment system as recited in claim 3, and further comprising a headphone amplifier connectable to an output of the plurality of outputs, the headphone amplifier having a plurality of amplifier outputs which are connectable to the plurality of sound transmitting devices.

5. The sound treatment system as recited in claim 1, and further comprising a plurality of the sound transmitting devices, for attachment to ankles and wrists of the body, wherein each sound transmitting device of the plurality of sound transmitting devices is electrically connected to an output of the plurality of outputs.

6. The sound treatment system as recited in claim 5, wherein a first output of the plurality of outputs delivers a first audio signal comprising a first combination of the audio segment and the at least one tone generated by the one or more applications, wherein a second output of the plurality of outputs delivers a second audio signal comprising a second combination of the audio segment and the at least one tone generated by the one or more applications, wherein the first combination is different than the second combination.

7. The sound treatment system as recited in claim 1, wherein the crystal is suspended over the speaker or piezo transducer.

8. The sound treatment system as recited in claim 7, wherein polyfilm is utilized to secure the crystal to the speaker or piezo transducer in the suspended state.

9. The sound treatment system as recited in claim 1, wherein the audio signal is delivered to the sound transmitting device in either a continuous or pulsed mode.

10. The sound treatment system as recited in claim 1, wherein the audio signal is delivered to a plurality of sound transmitting devices either simultaneously or sequentially, wherein the plurality of sound transmitting devices comprise the sound transmitting device.

11. A sound treatment system comprising:
one or more applications running on at least one processor and communicatively coupled to an audio board, the one or more applications analyzing frequencies of an audio segment to identify a dominant frequency and a harmonic frequency of the audio segment, the one or more applications generating at least one tone at one or more of the dominant frequency, the harmonic frequency, a multiple of the dominant frequency, and a multiple of the harmonic frequency, the one or more applications combining the audio segment and the at least one tone into an audio signal and transmitting the audio signal to the audio board;
the audio board comprising a plurality of outputs;
a sound transmitting device electrically connectable to an output of the plurality of outputs, wherein the sound transmitting device comprises a speaker or piezo transducer for transmitting the audio signal received from the output, the speaker or piezo transducer being adjacent to crystal which is vibrationally responsive to the audio signal;
the audio board transmitting the audio signal to the sound transmitting device through the output to create a harmonic resonance and a sympathetic vibration in the crystal, wherein the crystal creates as it vibrates an additional tone at a frequency, wherein the vibrating crystal also produces a piezoelectric current, wherein the audio signal, the additional tone and the piezoelectric current together cause a corresponding harmonic response in targeted organs and tissues of the body on which the sound transmitting device carrying the crystal is disposed by delivery of a supercharged electrical signal through acupuncture pulse or meridian points of the body.

12. The sound treatment system of claim 11, wherein the at least one tone comprises one or more of a sine waveform, a square waveform, a triangle waveform, and a sawtooth waveform.

13. The sound treatment system of claim 11, wherein the one or more of the dominant frequency, the harmonic frequency, a multiple of the dominant frequency and a multiple of the harmonic frequency includes one or more of a division of the dominant frequency and a division of the harmonic frequency.

* * * * *